(12) United States Patent
Kavusi et al.

(10) Patent No.: US 8,648,016 B2
(45) Date of Patent: Feb. 11, 2014

(54) ARRAY WITH EXTENDED DYNAMIC RANGE AND ASSOCIATED METHOD

(75) Inventors: Sam Kavusi, Menlo Park, CA (US);
Michaela Laupheimer, Erbach (DE);
Christoph Lang, Cupertino, CA (US)

(73) Assignee: Robert Bosch GmbH, Stuttgart (DE)

(*) Notice: Subject to any disclaimer, the term of this patent is extended or adjusted under 35 U.S.C. 154(b) by 573 days.

(21) Appl. No.: 12/701,712

(22) Filed: Feb. 8, 2010

(65) Prior Publication Data
US 2011/0195853 A1   Aug. 11, 2011

(51) Int. Cl.
*C40B 30/04* (2006.01)

(52) U.S. Cl.
USPC .......................................................... 506/9

(58) Field of Classification Search
USPC .......................................................... 506/9
See application file for complete search history.

(56) References Cited

U.S. PATENT DOCUMENTS

| | | | |
|---|---|---|---|
| 6,183,972 B1 * | 2/2001 | Kuo et al. | 435/7.1 |
| 6,551,788 B1 | 4/2003 | Bell | |
| 2006/0019404 A1 | 1/2006 | Blatt et al. | |
| 2007/0250271 A1 * | 10/2007 | Leonard et al. | 702/19 |
| 2008/0131892 A1 * | 6/2008 | Becker et al. | 435/6 |
| 2008/0311677 A1 | 12/2008 | Chin et al. | |
| 2011/0091870 A1 * | 4/2011 | Lang et al. | 435/6 |

FOREIGN PATENT DOCUMENTS

| | | |
|---|---|---|
| EP | 0987551 A2 | 3/2000 |
| WO | 2008145722 A1 | 12/2008 |

OTHER PUBLICATIONS

Reed et al., ("Use of Coefficient of variation in Assessing Variability of Quantitative Assays", Clinical and Diagnostic Laboratory Immunology, vol. 9, No. 6, pp. 1235-1239).*
International Search Report in corresponding PCT application (i.e., PCT/US2011/023863), mailed Apr. 20, 2011 (4 pages).
S. F. Kingsmore, "Multiplexed protein measurement: technologies and applications of protein and antibody arrays," Nature Reviews Drug Discovery, No. 4, pp. 310-320, 2006 (Printed on 23 pages).
Patrick Domnanich, Ursula Sauer, Johanna Pultar, and Claudia Preininger, "Protein microarray for the analysis of human melanoma biomarkers," Sensors and Actuators B: Chemical, vol. 139, pp. 2-8 (2009).
N. Ohmura, Y. Tsukidate, H. Shinozaki, S. J. Lackie, and H. Saiki, "Combinational Use of Antibody Affinities in an Immunoassay for Extension of Dynamic Range and Detection of Multiple Analytes," Analytical Chemistry, vol. 75, No. 1, pp. 104-110, 2003.

(Continued)

*Primary Examiner* — Ardin Marschel
*Assistant Examiner* — Richard L Manteuffel
(74) *Attorney, Agent, or Firm* — Maginot, Moore & Beck (57) ABSTRACT

A system and method of quantitating the concentration of a molecule of interest in one embodiment includes establishing a plurality of test environments at a plurality of test sites, each of the plurality of test environments associated with one of a plurality of response curves, each of the plurality of response curves different from the other of the plurality of response curves, storing a combined response curve resulting from a summation of the plurality of response curves, exposing the plurality of test sites to a sample having a concentration of a molecule of interest, obtaining a plurality of quantitation signals, each of the plurality of quantitation signals associated with one of the plurality of test sites, associating a summation of the plurality of quantitation signals with the stored combined response curve, and generating a signal related to the concentration of the molecule of interest based upon the association.

10 Claims, 7 Drawing Sheets

(56) References Cited

OTHER PUBLICATIONS

A.P. Drabovich, V. Okhonin, M. Berezovski, and S. N. Krylov, "Smart Aptamers Facilitate Multi-Probe Affinity Analysis of Proteins with Ultra-Wide Dynamic Range of Measured Concentrations," Journal of the American Chemical Society), vol. 129, No. 23, pp. 7260-7261 and S1-S5, 2007 (2 pages plus 5 pages of Supporting Materials).

M. L. Yarmush, K.P. Antonsen, S. Sundaram, and D.M. Yarmush, "Immunoadsorption: Strategies for Antigen Elution and Production of Reusable Adsorbents," Biotechnology Progress, vol. 8, No. 3, pp. 168-178, 1992.

D. R. Jackola et al., "Entropy-favored human antibody binding reactions with a non-infectious antigen," Molecular Immunology, vol. 45, No. 5, pp. 1494-1500, 2008.

J.J. Gooding et al., "Electrochemical modulation of antigen-antibody binding," Biosensors and Bioelectronics, vol. 20, No. 2, pp. 260-268, 2004.

M. L. O'Grad, K. Parker, "Dynamic Control of Protein-Protein Interactions," Langmuir, vol. 24 (1), pp. 316-322, 2008.

R. J. Heaton, A.W. Peterson, R.M. Georgiadis, "Electrostatic surface plasmon resonance: Direct electric field-induced hybridization and denaturation in monolayer nucleic acid films and label-free discrimination of base mismatches," Proceedings of the National Academy of Sciences, vol. 98, No. 7., pp. 3701-3704, 2001.

\* cited by examiner

ARRAY WITH EXTENDED DYNAMIC RANGE AND ASSOCIATED METHOD

FIELD

This invention relates to diagnostic tests and more specifically to affinity based diagnostic tests.

BACKGROUND

Diagnostic tests that can be performed at the point of care of an individual, such as at the bedside of a patient, at a care provider location, or at the home of the patient, are becoming increasingly popular. Diagnostic tests include tests directed to identifying biomarkers such as Nucleic Acid, protein, and small molecules. Many of the diagnostic testing devices incorporate affinity based sensors which are considered to be the state-of-the-art in detection of biomarkers.

Affinity based biosensors function according to a "key-lock" principal in which a molecule with very high association factor to the biomarker of interest is used for detection. For example, a pregnancy test kit may incorporate a monoclonal antibody specific to a β-subunit of hCG (βhCG). The antibody is conjugated with a tag, e.g., gold, latex, or a fluorophore, which is used for detection. If the targeted molecule binds with the conjugated antibody, the tagged key-lock pair will be detectable such as by a visible test line.

Figure 1:
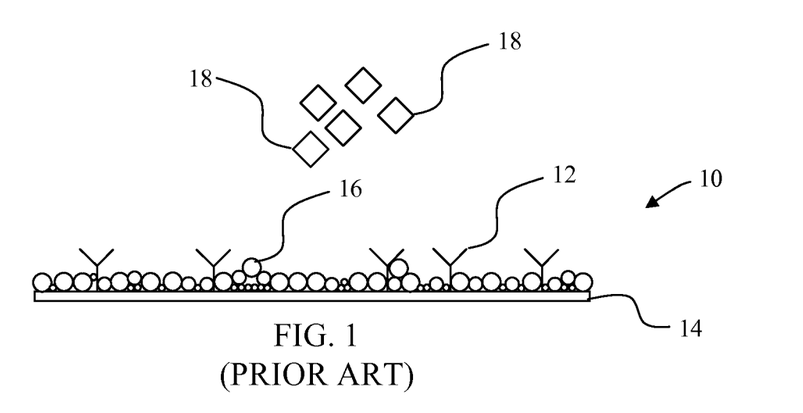
FIG. 1 depicts a schematic of a prior art test site within an ELISA array with an antibody and blockers formed on a substrate as a sample is added to the test site.
Figure 2:
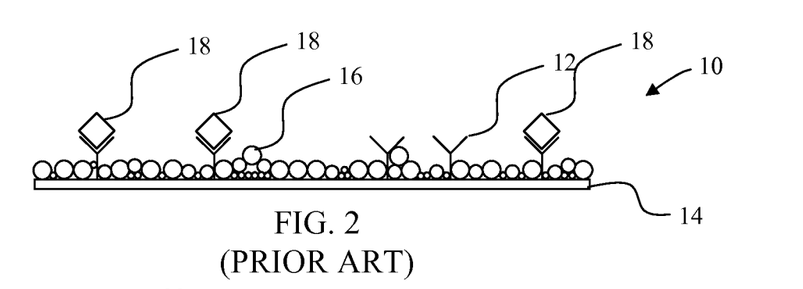
FIG. 2 depicts the test site of FIG. 1 with a molecule of interest bound to some of the antibodies of FIG. 1 after the test site has been incubated and washed.

ELISA plates and microarrays (e.g., Nucleic Acid, peptide, and protein) incorporate a similar principal. FIG. 1 depicts an ELISA assay 10 wherein antibodies 12 are immobilized on a substrate 14. The substrate 14 may be positioned within a well (not shown). A blocker 16 is provided to cover the surface of the substrate around the antibody 12. In a typical ELISA assay, a sample 18 is then added to the well in which the primary antibody 12 is immobilized. Next, the sample is incubated for some time. During incubation, the blocker 16 prevents the molecules of interest in the sample from binding to the surface of the substrate 14 in order to avoid false binding. During incubation, some of the molecules of interest 18 become bound with some of the antibodies 12 as depicted in FIG. 2. After incubation, the remaining sample is washed to remove the unbound molecules 18.

Figure 3:
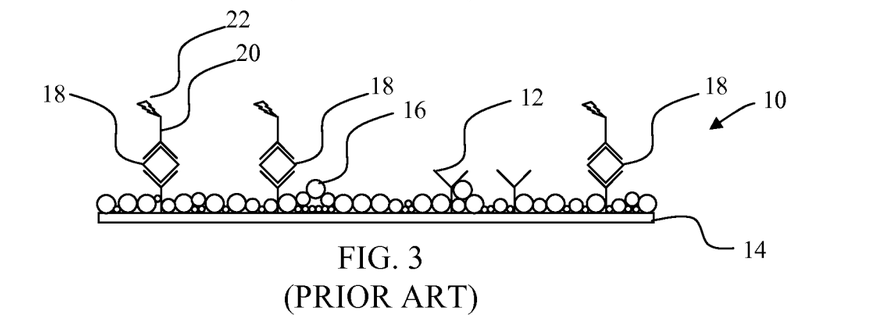
FIG. 3 depicts the test site of FIG. 2 after a labeled secondary antibody has been added and the test site has again been incubated and washed so that the labeled secondary is bound to the bound molecules of interest.

Subsequently, a secondary antibody 20 with a bound label 22 is added to the well, incubated, and washed resulting in the configuration of FIG. 3. As depicted in FIG. 3, the labeled secondary antibodies 20 are bound to the molecules of interest 18 that are in turn bound to the antibodies 12. Accordingly, the number of labels 22 bound by the antibodies 20 to the molecule of interest 18 is proportional to the concentration of the target molecule. Depending on the type of label used, the number of labels can be finally detected using colorimetry, amperometry, magnetometry, voltammetry, luminescence, or fluorescence detection. Other label-free antibody processes such as surface plasmon resonance may alternatively be used.

The quality of the diagnostic tests discussed above can be assessed using Limit of Detection (LoD) and Limit of Quantitation (LoQ) analysis. LoD, which is the minimum concentration of target molecules needed in order to create a large enough quantity of complexes that can be recognized by the available means of detection, is affected by the mutual affinity between a probe molecule and a target molecule, the density of probe molecules, incubation conditions, and the level of background and noise in the detection mechanism. As reported by Burtis, et al., "Tietz Textbook of Clinical Chemistry and Molecular Diagnostics," *Elsevier Saunders,* 2005, the LoD for a particular assay is generally considered to be the concentration of target molecules that produces a signal 2-3 times greater than the average background signal.

The LoQ metric includes both an upper limit and a lower limit. The upper and lower limits as defined by Burtis, et al. "Tietz Textbook of Clinical Chemistry and Molecular Diagnostics," *Elsevier Saunders,* 2005, are the highest and lowest concentrations, respectively, that can be quantitatively measured within an acceptable total error for the particular assay. Generally, the acceptable error for a particular assay in the United States is defined by the Food and Drug Administration based upon the standard deviation of so-called "gold standard tests".

The range of concentrations between the lower LoQ and the upper LoQ for a particular assay is the dynamic range of the assay. The lower LoQ is related to the LoD which, as discussed above, is related to the affinity probe molecule density on the substrate. Thus, a high affinity probe molecule density is incorporated in many assays so as to increase the sensitivity of the particular assay. The upper LoQ, however, is typically a function of the maximum density or concentration of probe molecules that can be achieved in a particular assay.

Figure 4:
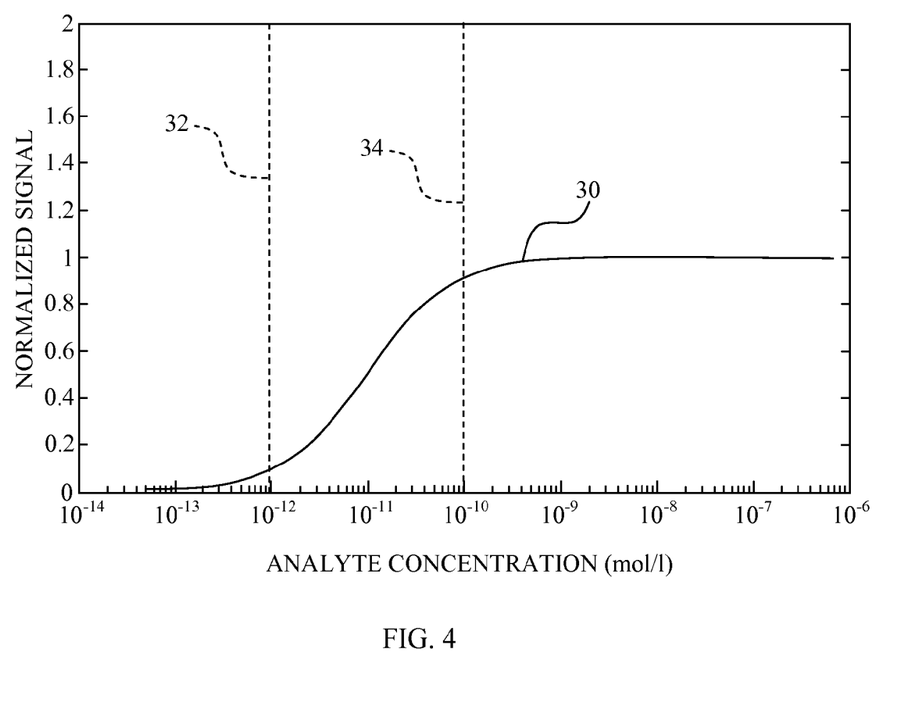
FIG. 4 depicts a response curve for a typical assay showing the normalized output signal of a system as a function of the concentration of an analyte of interest in a tested sample.

Given a particular concentration of affinity probe molecules, the normalized signal obtained from a particular assay does not vary linearly with the concentration of the analyte of interest. By way of example, FIG. 4 depicts a response curve (RC). A "response curve" as that term is used herein is a curve showing the relationship between various concentrations of a molecule of interest in a plurality of samples and a plurality of quantitation signals obtained from the plurality of samples for a particular assay. In FIG. 4, a typical signal response versus target concentration for a particular assay is depicted as a response curve 30. Within the range of signals of FIG. 4, a lower LoQ is defined by the line 32 at about $10^{-12}$ mol/l while the upper LoQ is defined by the line 34 at about $10^{-10}$ mol/l. Between the lower LoQ 32 and the upper LoQ 34, the response curve 30 is shaped like an ogee. The dynamic range of the assay which produces the response curve 30 of FIG. 4 is about two orders of magnitude. The dynamic range of a typical assay is generally between 1 to 3 orders of magnitude.

The dynamic range of a particular assay limits the usefulness of the assay in applications wherein the expected variation in tested samples is several orders of magnitude. By way of example, detectable proteins in human serum range in abundance from grams to tenths of picograms per milliliter. Furthermore, serum protein abundance can change by as much as 10,000-fold on stimulation. As reported by S. F. Kingsmore, "Multiplexed protein measurement: technologies and applications of protein and antibody arrays," *Nature Reviews Drug Discovery*, No. 4, pp. 310-320, 2006, many of the proteins that are most frequently measured, such as acute phase reactant pentraxins or chemokines, also exhibit large variations. Accordingly, the expression range for many biomolecules can span 6 orders of magnitude or more and a convenient assay should have an equal dynamic range while the dynamic range of a typical assay is generally between 1 to 3 orders of magnitude.

In multiplexed assays and microarrays the issue of narrowly limited dynamic range is especially relevant as detection of multiple biomarkers is critical for improving diagnostics. Microarrays, however, fall short of achieving the levels of quantification that established optimized tests, e.g., ELISA, can realize, even in conjunction with other time consuming lab techniques, e.g., serial dilution. Accordingly, while microarrays are heavily used and are experiencing an exponential growth, such usage is primarily directed to detection of molecules of interest rather than in quantification of molecules of interest. The use of multiplexed assays and microarrays even as detection mechanisms, however, is limited. For example, even healthy individuals carry markers which, when present in greater concentrations, can indicate the presence of a disease.

In response to limited upper LoQs in earlier assays, some manufacturers have developed substrates which allow for higher densities of the immobilized probe molecule and thus higher dynamic range. Such substrates generally include a three dimensional structure which, while providing a greater dynamic range, may also increase the assay variation. Some of such approaches result in the binding kinetics and stability of probe molecules and may even cause reduction in dynamic range.

Another approach to increasing the dynamic range of assays is to perform a series of dilutions on a sample such that one of the diluted samples provides a target concentration that is within the dynamic detection range of an assay. Such an approach has been reported by Patrick Domnanich, et al. "Protein microarray for the analysis of human melanoma biomarkers," *Sensors and Actuators B: Chemical, Vol.* "In Press, Corrected Proof", 2008. This simple yet effective approach has the disadvantage of requiring a considerable number of additional steps (including multiple dilutions and multiple runs of the actual assay) which add to the test time and increases costs and operating expenses.

Recently, other solutions have been proposed to increase the dynamic range of an assay. One such solution for a point of care device disclosed in U.S. Patent Application Publication No. 2006/0019404 A1 includes the use of two strips with different dynamic ranges. Different dynamic ranges can be achieved by using different antibodies and, by combining the results, a wider dynamic range for the assay can be achieved. Other solutions reported by N. Ohmura, et al., "Combinational Use of Antibody Affinities in an Immunoassay for Extension of Dynamic Range and Detection of Multiple Analytes," *Analytical Chemistry*, Vol. 75, No. 1, pp. 104-110, 2003, and A. P. Drabovich, et al., "Smart Aptamers Facilitate Multi-Probe Affinity Analysis of Proteins with Ultra-Wide Dynamic Range of Measured Concentrations," *Journal of the American Chemical Society*, Vol. 129, No. 23, pp. 7260-7260, 2007, include the use of two or more probe molecules, either antibodies or aptamers, with different affinities for the analyte in order to extend the dynamic range. Such approaches require an overlap between the dynamic ranges of the different probe molecules used and are thus limited by the availability of multiple antibodies or aptamers having the desired affinities.

A need exists for a device and method of performing a quantization assay incorporating low cost antibodies. A further need exists for low cost assays including multiplexed assays, protein arrays, lateral flow devices, sandwich assays, competitive assays, or bead based arrays which provide accurate quantization results and a method of using such arrays. Methods and devices which provide relatively linear results would be a further benefit.

SUMMARY

In accordance with one embodiment, a system and method of quantitating the concentration of a molecule of interest includes establishing a plurality of test environments at a plurality of test sites, each of the plurality of test environments associated with one of a plurality of response curves, each of the plurality of response curves different from the other of the plurality of response curves, storing a combined response curve resulting from a summation of the plurality of response curves, exposing the plurality of test sites to a sample having a concentration of a molecule of interest, obtaining a plurality of quantitation signals, each of the plurality of quantitation signals associated with one of the plurality of test sites, associating a summation of the plurality of quantitation signals with the stored combined response curve, and generating a signal related to the concentration of the molecule of interest based upon the association.

In accordance with another embodiment, a method of quantitating the concentration of a molecule of interest includes establishing a first test environment at a first test site, establishing a second test environment at a second test site such that a response curve for the second site is different from a response curve of the first site, storing a combined response curve resulting from a summation of the response curve for the second site and the response curve of the first site, exposing the first test site and the second test site to a sample having a concentration of a molecule of interest, obtaining a first quantitation signal from the first test site, obtaining a second quantitation signal from the second test site, combining the first quantitation signal and the second quantitation signal, associating the combined first quantitation signal and second quantitation signal with the stored response curve, and generating a signal related to the concentration of the molecule of interest based upon the association.

DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
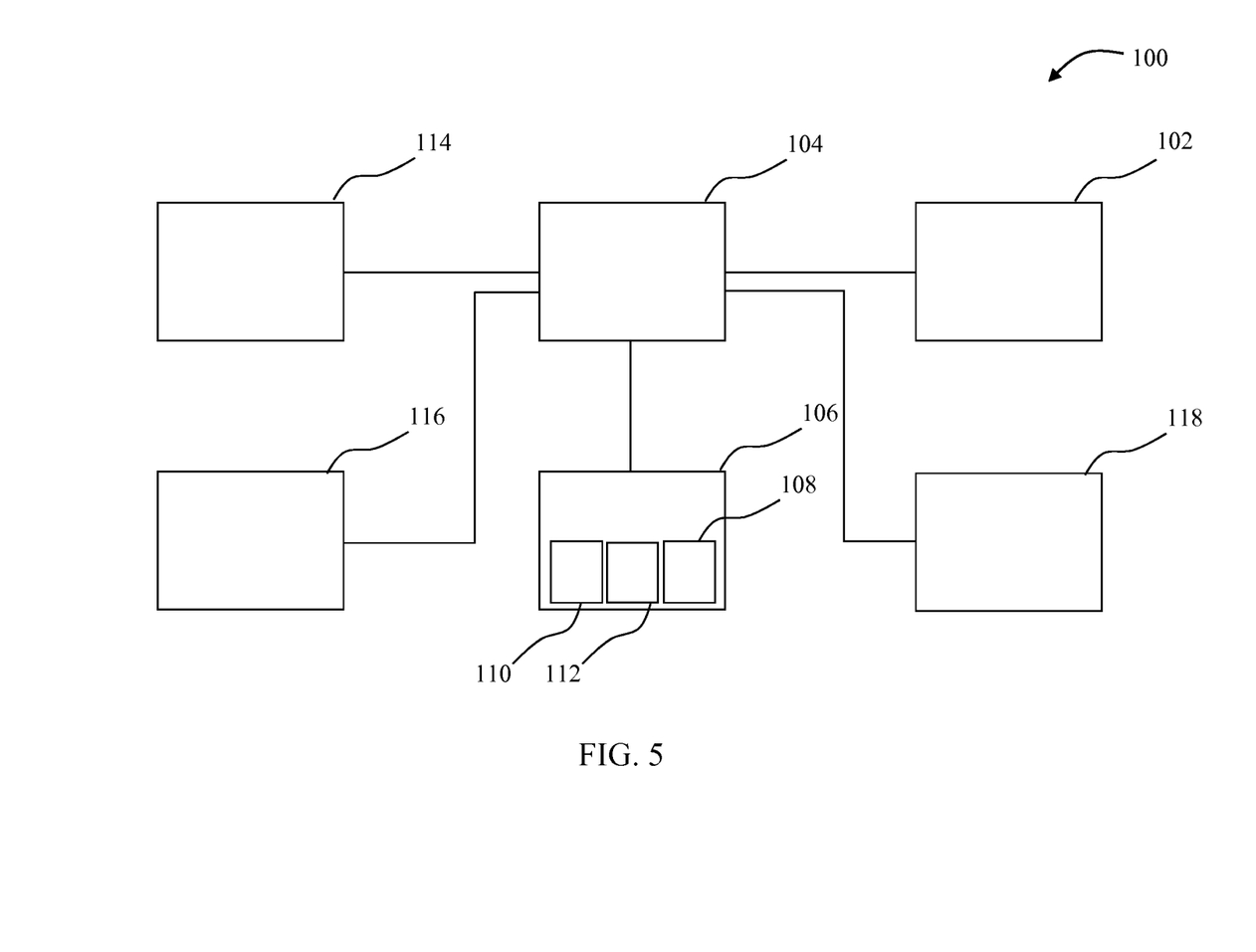
FIG. 5 depicts a multi-site biosensor system configured to expose a single sample to different environmental conditions allowing determination of the concentration of a molecule of interest in a sample over an extended range of concentrations.

Referring to FIG. 5, there is depicted a representation of a multisite biosensor system generally designated 100. The biosensor system 100 includes an I/O device 102, a processing circuit 104 and a memory 106. The I/O device 102 may include a user interface, graphical user interface, keyboards, pointing devices, remote and/or local communication links, displays, and other devices that allow externally generated information to be provided to the biosensor system 100, and that allow internal information of the biosensor system 100 to be communicated externally.

The processing circuit 104 may suitably be a general purpose computer processing circuit such as a microprocessor and its associated circuitry. The processing circuit 104 is operable to carry out the operations attributed to it herein.

Within the memory 106 are various program instructions 108. The program instructions 108, some of which are described more fully below, are executable by the processing circuit 104 and/or any other components as appropriate. Affinity databases 110 and response curve (RC) databases 112 are also located within the memory 106.

The biosensor system 100 further includes environment control equipment 114, environment detector suite 116, and a label reader 118. The label reader 118 may be included in a single device along with the other components of the system 100.

Alternatively, one or more of the components of the system 100 may be provided as a separate device which may be remotely located from the other components of the system 100.

Figure 6:
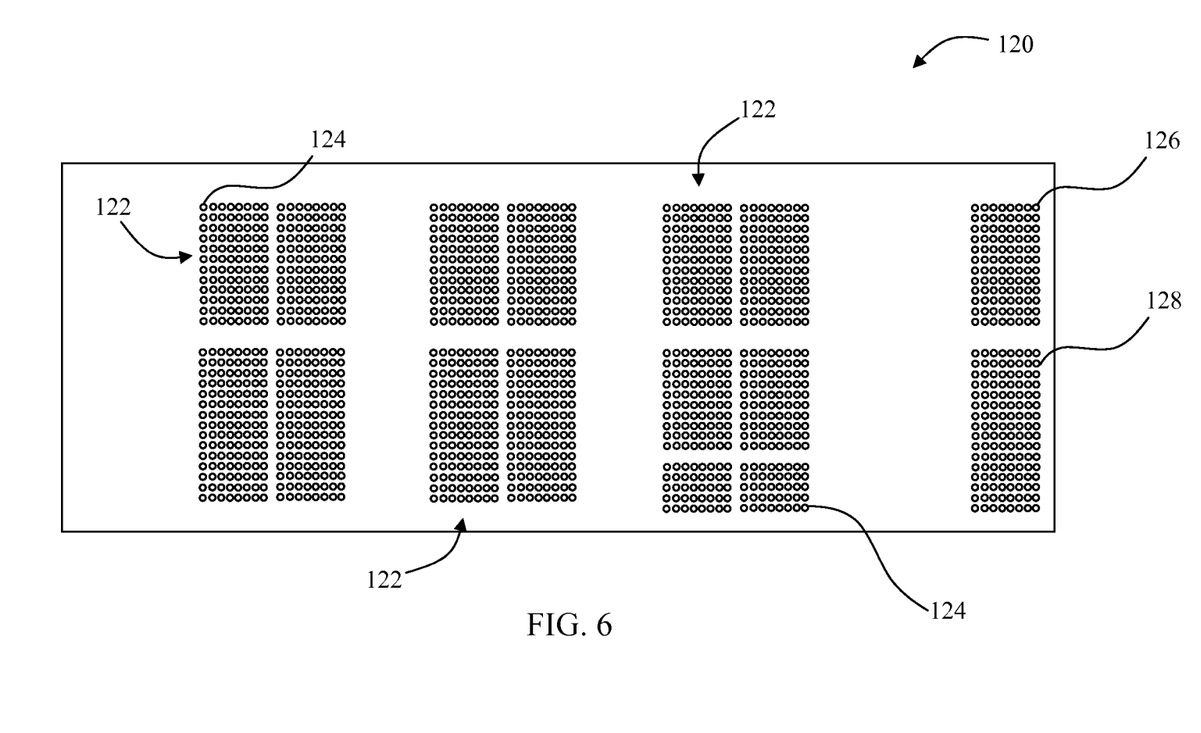
FIG. 6 depicts a platform for providing a number of different test sites in the form of a microarray.

The environment control equipment 114 is configured to establish and maintain environmental conditions, in this example, within a microarray 120 depicted in FIG. 6. Various methods may be used to form the microarray platform 120. By way of example, U.S. Pat. No. 5,807,522 discloses a method for forming microarrays. The microarray platform 120 includes a number of different subarrays 122. The subarrays 122 include a number of test sites 124. The number of subarrays 122 as well as the number of test sites 124 within each of the subarrays 122 may be varied within the scope of the invention. The microarray 120 further includes two calibration arrays 126 and 128. In some embodiments, the processor 104 may also be positioned on the microarray 120.

As reported by D. R. Jackola et al., "Entropy-favored human antibody binding reactions with a non-infectious antigen," *Molecular Immunology*, Vol. 45, No. 5, pp. 1494-1500, 2008, temperature changes the binding efficiencies of some molecules. Accordingly, in the embodiment of FIG. 5, the environment control equipment 114 is operable to establish a temperature profile within the microarray platform 120. The precise temperature within each of the test sites 124 and the calibration arrays 126 and 128 may be detected by the detector suite 116.

The test sites 124 and the calibration arrays 126 and 128 are prepared with a capturing agent effective for capturing a biomolecule of interest. Further details regarding the biosensor system 100 are provided with reference to the procedure 130 of FIG. 7. The processor 104 executes the program instructions 108 to execute at least some of the procedure 130 of FIG. 7. In different embodiments, the procedure 130 may be modified to include more or fewer steps depending upon the specific criterion.

Figure 7:
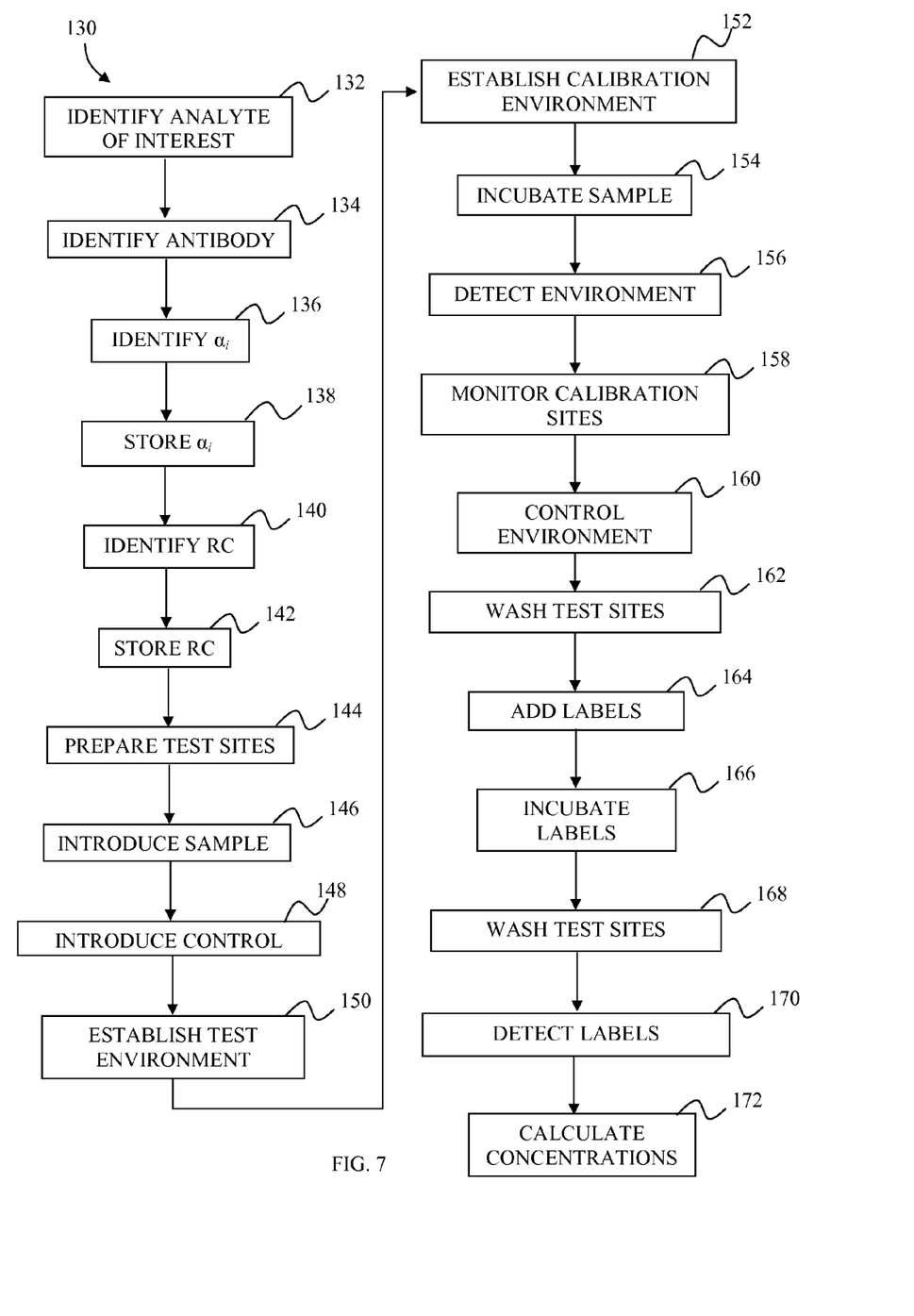
FIG. 7 depicts a procedure that can be used to establish different test environments at various test sites on a platform so as to expose a sample to multiple test environments.

At block 132, a molecule of interest is identified and then a probe molecule with an affinity for the molecule of interest, such as an antibody, a synthetic peptide, aptamer, etc., is identified (block 134). A binding efficiency coefficient for the molecule of interest ($a_i$) with the identified antibody is then identified for at least two different environmental conditions (block 136) and stored in one of the affinity databases 110 (block 138).

The response curves associated with the at least two binding efficiency coefficients are then identified (block 140) and stored in the RC databases 112 (block 142). At block 144, the microarray platform 120 is prepared by depositing the desired amount of the selected capturing agent in each of the test sites 124 and the calibration sites 126 and 128. In alternative embodiments, a subset of the test sites 124 and the calibration site 126 may be prepared with a first capturing agent while another subset of the test sites 124 and the calibration test site 128 may be prepared with a second capturing agent so as to allow two separate tests to be conducted within a single microarray platform 120. Additional configurations within a single microarray platform 120 may also be used. By way of example, each of the test sites within one of the subarrays 122 may be prepared with the same capturing agent while each of the subarrays 122 includes a different capturing agent.

Once the microarray platform 120 is prepared, a sample is introduced into the selected set of test sites 124 (block 146). Prior to introduction, the sample may first be prepared by processes such as filtration and amplification, including the addition of reagents and other control preprocessing. A control substance is also introduced to the calibration sites 126 and 128 (block 148).

If not already established, the environment within each of the selected set of test sites 124 is controlled to establish, within each of the selected set of test sites 124, a different test environment (block 150). In this example, the environmental condition that is controlled is temperature. Accordingly, a thermal profile is established across the microarray platform 120. Depending upon the particular embodiment, this may be accomplished by providing a unique heater/cooler for each of the selected set of test sites 124 or subarrays 122. In other embodiments, heat is applied at one end of the microarray platform 120 and a heat sink is thermally attached to the opposite end of the microarray platform 120 to establish a thermal gradient across the microarray platform 120. The environment at the calibration sites 126 and 128 is also controlled (block 152).

The sample and control substances are then incubated at the established test/calibration environment for a predetermined time (block 154). During the incubation, the actual test environment within each of the selected set of test sites 124 is monitored by the environment detector suite 116 and data indicative of the established test environment is provided to the processing circuit 104 (block 156). Additionally, the actual calibration environment within each of the calibration sites 126 and 128 is monitored by the environment detector suite 116 and data indicative of the established calibration environment is provided to the processing circuit 104 (block 158). Bonding activity at the calibration sites 126 and 128 is also monitored and data indicative of the activity is provided to the processing circuit 104. The bonding activity at the calibration sites 126 and 128 may be analyzed by the processing circuit 104 to modify control of the test site environment (block 160). In other embodiments, the calibration sites 126 and 128 are used to reconstruct the actual environment to correct for errors, e.g., at block 172.

When the sample has been sufficiently incubated, the test sites 124 are washed (block 162) and a labeled secondary antibody is introduced into the selected set of test sites 124 (block 164) and incubated (block 166). The selected set of test sites 124 are then washed (block 168) and the labels remaining in the test sites 124 are detected by the label reader 118 (block 170). Based upon the signals associated with the number of labels remaining in the selected set of test sites 124, the concentration of the molecule of interest within the sample is calculated by the processing circuit 104 (block 172).

Calculation of the concentration of the molecule of interest is possible because the test environments for the test sites 124 are controlled to provide a combined response curve having a combined minimum LoQ that is at or below the minimum concentration which is desired to be quantitated and a combined maximum LoQ that is at or above the maximum concentration which is desired to be quantitated. Additionally, the test environments for the test sites 124 are controlled such that the ogee of the response curve associated with a particular test site 124 overlaps the ogee of the response curve of at least one other test site 124 throughout the concentration range of interest. The foregoing may be understood with reference to FIG. 8.

Figure 8:
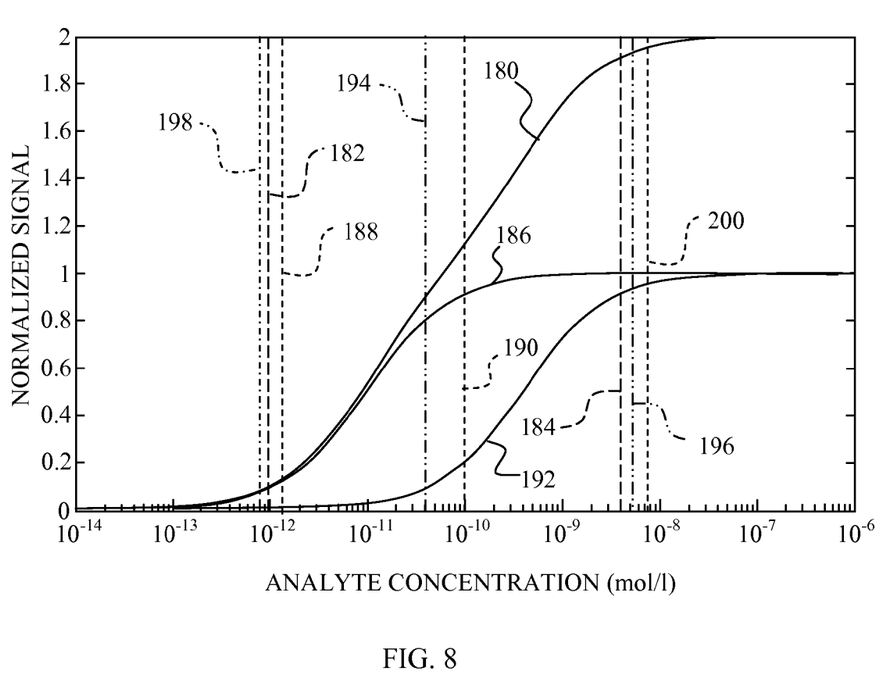
FIG. 8 depicts a combined response curve showing the normalized output signal of a system as a function of the concentration of an analyte of interest in a tested sample when the response curves for two sites with different test environments are summed.

FIG. 8 depicts a combined response curve 180 that extends substantially linearly throughout a concentration range of interest that is bounded by a minimum concentration 182 and a maximum concentration 184. The concentration range of interest is larger than the dynamic range of any single test site 124 for a given test environment.

By way of example, the response curve 186 is associated with a first test site 124. The response curve 186 has a minimum LoQ 188 and a maximum LoQ 190. The minimum LoQ 188 is greater than the minimum concentration 182 while the maximum LoQ 190 is much less than the maximum concentration 184. Accordingly, the test site 124 associated with the response curve 186 can be used to provide reliable quantitation of samples with a concentration slightly above the minimum concentration 182 of the concentration range of interest and much less than the maximum concentration 184. Accordingly, the test site 124 associated with the responses curve 186 cannot be used to provide reliable quantitation of concentrations throughout the concentration range of interest.

With continued reference to FIG. 8, the response curve 192 has a minimum LoQ 194 and a maximum LoQ 196. The minimum LoQ 194 is less than the maximum LoQ 190 for the response curve 186, while the maximum LoQ 196 is greater than the maximum concentration 184. Accordingly, the test site 124 associated with the response curve 192 can be used to provide reliable quantitation of samples with a concentration at the maximum LoQ 190 for the response curve 186 and up to concentrations that are at the maximum concentration 184 of the concentration range of interest.

Thus, quantitation of samples within the concentration range of interest, which extends from the minimum concentration 182 to the maximum concentration 184, is possible by summing the signals obtained from the test sites 124 associated with the response curves 186 and 192. The concentration associated with the combined signal is obtained using the response curve 180, which is a summation of the response curves 186 and 192. Because the response curve 180 is a summation of the response curves 186 and 192, the minimum LoQ 198 for the response curve 180 will be a concentration slightly less than the minimum LoQ for the most sensitive response curve (response curve 186), while the maximum LoQ 200 for the response curve 180 will be a concentration slightly greater than the maximum LoQ for the least sensitive response curve (response curve 192).

Therefore, by carefully controlling the environment at each of a plurality of test sites 124, a combined output signal may be obtained which has a relatively linear relationship to the concentration of a molecule of interest. Moreover, while only two response curves were needed to fully cover the concentration range of interest in FIG. 8, the test environment at additional sites may be further controlled to provide response curves that are higher than the response curve 192 (to the right as depicted in FIG. 8), or lower than the response curve 186 (to the left as depicted in FIG. 8) if increased dynamic range is desired.

An important consideration in selecting the environmental factor(s) controlled at block 150 of FIG. 7 is to select two or more test environments that result in response curves that overlap in the desired manner. An "overlap" is a range of concentrations which are within the dynamic range of at least two response curves. Linearity of a combined response curve can be optimized by controlling the test environment at different test sites 124 to provide an overlap as depicted in FIG. 8.

Figure 9:
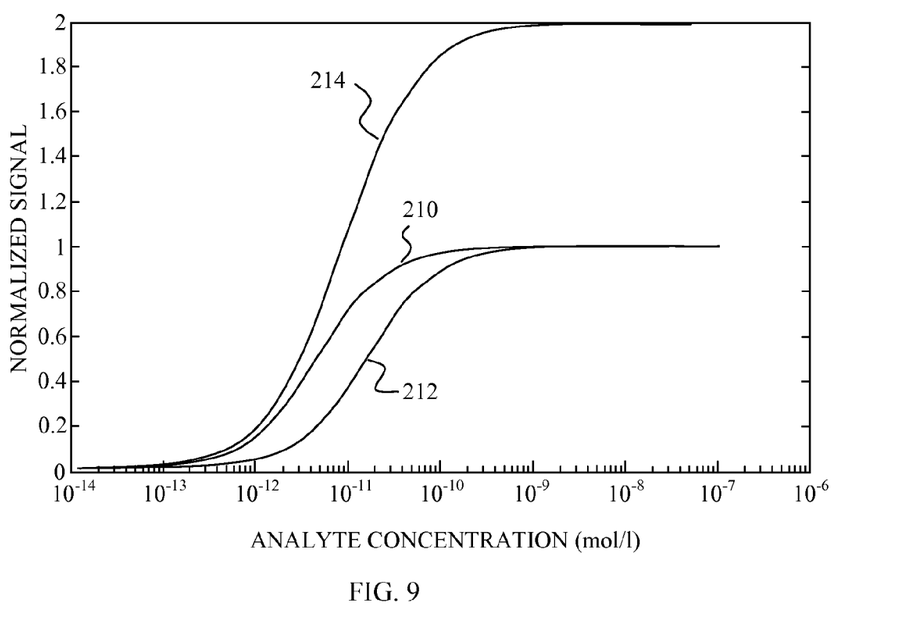
FIG. 9 depicts a combined response curve showing the normalized output signal of a system as a function of the concentration of an analyte of interest in a tested sample when the response curves for two sites with low affinity modulation are summed.

As the overlap is increased, the combined response curve increases in slope. By way of example, FIG. 9 depicts a response curve 210 and a response curve 212. The affinity at the test site associated with the response curve 212 is only slightly less than the affinity at the test site associated with the response curve 210. This low modulation of affinity results in a combined response curve 214 that exhibits an increased slope as compared to the response curve 180. The dynamic range of the combined response curve 214, however, is much less than the dynamic range of the combined response curve 180. Accordingly, decreasing the overlap allows for a greater dynamic range for a fixed number of test site environments.

Figure 10:
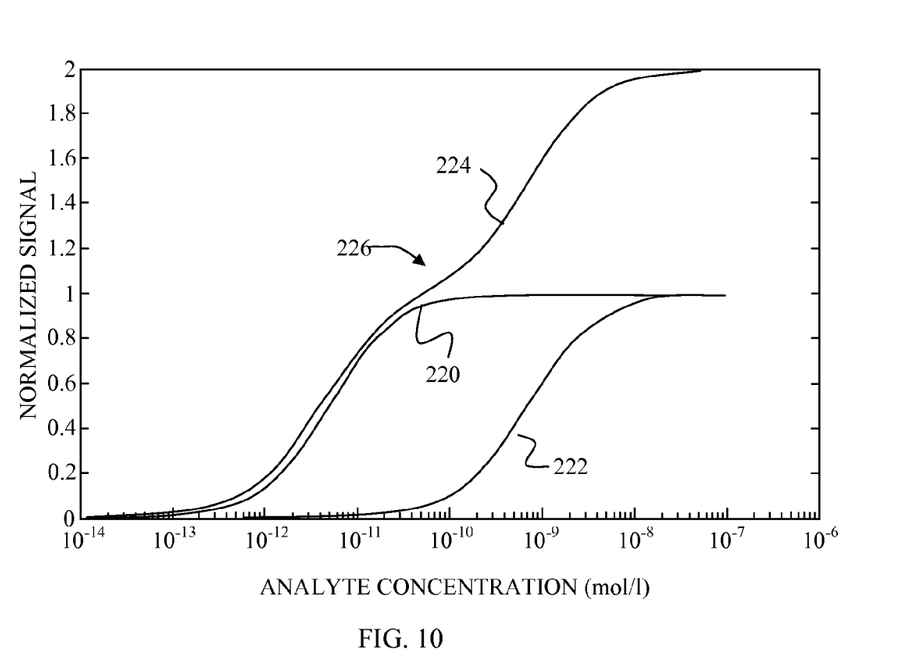
FIG. 10 depicts a combined response curve showing the normalized output signal of a system as a function of the concentration of an analyte of interest in a tested sample when the response curves for two sites with high affinity modulation are summed.

As the overlap is decreased, however, the slope of the resulting combined response curve is reduced. By way of example, FIG. 10 depicts a response curve 220 and a response curve 222. The affinity at the test site associated with the response curve 222 is significantly less than the affinity at the test site associated with the response curve 220. This high modulation of affinity results in a combined response curve 224 that exhibits a decreased slope as compared to the response curve 180. The dynamic range of the combined response curve 224, moreover, is greater than the dynamic range of the combined response curve 180. The combined response curve 224, however, also has a flattened region 226. In the flattened region 226, the potential error in the quantitation of analyte concentration is increased. Providing another test site with an affinity greater than the affinity of the test site associated with the response curve 222 and less than the affinity of the test site associated with the response curve 220, however, can eliminate the flattened region 226.

In the foregoing example, the temperature within each of the test sites 124 was controlled to provide different binding efficiencies. In embodiments incorporating CMOS technology, a temperature gradient within the chip can be established using on-chip resistors such as polysilicon resistors or integrated Peltier elements. Low power on-chip temperature sensors can be used to accurately measure the temperature within each of the test sites. A multisite biosensor can thus be implemented on a printed circuit board, glass, plastic substrate, or on a CMOS chip with gold, glass, epoxy, polymer, or gel coating, or even in a well plate such as a 96 well plate. If desired, control, readout, and also sensing for the control can be provided in the printed circuit board or CMOS chip. CMOS technology allows multiple sensing sites to be fabricated in close proximity. This assists in maintaining uniformity of non-controlled environmental factors amongst the test sites. The chip can be part of a system using stand alone microfluidics or a capillary principle or may be used with a separately provided device. The signal estimation and the assay data can be hard coded on the CMOS chip if desired.

Temperature is not the only environmental factor which can be used to establish different test environments. The electric field in which incubation is conducted has been shown to modify the binding efficiencies of molecules as reported by J. J. Gooding et al., "Electrochemical modulation of antigen-antibody binding, " *Biosensors and Bioelectronics*, Vol. 20, No. 2, pp. 260-268, 2004, M. L. O'Grady, et al., "Dynamic Control of Protein-Protein Interactions," *Langmuir*, Vol. 24 (1), pp. 316-322, 2008, R. J. Heaton et al., "Electrostatic surface plasmon resonance: direct electric field-induced hybridization and denaturation in monolayer nucleic acid films and label-free discrimination of base mismatches," *Proceedings of National Academy of Science*, Vol. 98, No. 7, pp. 3701-3704, 2001, and *I. Wong et al.*, "Dynamic control of biomolecular activity using electrical interfaces," *Soft Matter*, Vol. 3, No. 3, pp 267-274, 2007.

In some embodiments, the electric field within each of the test sites may be controlled to be different from the electric field within each of the other of the test sites. The electric field can be used to modify, e.g., local concentrations, pH, etc. The underlying mechanisms include electrolysis and ion attraction. The use of an AC signal may further provide local mixing by creating movement of ions within the sample, e.g., through electrohydrodaynamic effects. Many voltage ranges which provide the foregoing effects are CMOS compatible. Accordingly, a CMOS chip with surface electrodes may be used. Depending upon the desired effect, one, two or more electrodes may be provided at a particular test site and either exposed or isolated from the test sample. Another fabrication method incorporates glass slides with electrodes (e.g., ITO, gold) or plastic or paper membrane with printed electrodes (e.g., carbon, gold, silver).

Another approach to controlling the test environment is through the use of magnetic beads and a controlled magnetic field. The magnetic beads are functionalized with molecules that have high affinity against a range of biomolecules, e.g., antibody, epoxy, Nucleic Acid, or aptamers. As the magnetic beads are moved across the sensor sites, different molecules will bind to them at different rates, thereby scraping the surfaces of the test sites and "cleaning" the test sites. Controlling the magnetic field within the test sites affects the extent of "cleaning" that occurs at each test site, thereby modifying the binding efficiency of different molecules depending upon the strength of the bonds formed between the molecules and the antibodies. An external magnet may be used in various embodiments to bias the magnetic field to the desired values since CMOS integrated coils can only generate moderate magnetic fields.

Another approach is to modulate the affinities using different pressure at different test sites while incubating/washing the spots since pressure can be used to modify affinities as reported by M. L. Yarmush, et al., "Immunoadsorption: strategies for antigen elution and production of reusable adsorbents," *Biotechnology Progress*, Vol. 8, No. 3, pp. 168-178, 1992. Pressure modification can be achieved in a fluidic setup.

The type of sensor or sensors incorporated into the label reader 118 will vary depending upon the particular label used. Various embodiments may thus use luminescence, fluorescence, colorimetric, electrochemical, impedance, and magnetic sensors. The sensors should be configured to allow isolation of the signal produced by a selected one or more test sites. Likewise, the sensors incorporated into the environment detector suite 116 may include IR sensors, and Hall sensors. AMR sensors or GMR sensors may be provided to monitor the density of magnetic beads on a test site surface. ISFETs or CMOS based charge detection circuits may be used in electrochemical embodiments.

The concentration of a molecule of interest can thus be obtained over a wide range of concentrations even if the range of concentrations exceeds the dynamic range that can be realized with a single test site. Moreover, the procedure 130 can be used in a variety of test site platforms including 96-well plates, plates with fewer or additional wells, microarray platforms, printed circuit board platforms, CMOS chip platforms, multiplexed assays, protein arrays, lateral flow devices, sandwich assays, competitive assays, bead based arrays or other appropriate platforms. The procedure 130 may further be used for the detection of a variety of molecules of interest as well as different types of molecules in addition to antibodies. By way of example, the procedure 130 may also be used for the detection of Nucleic Acid, protein, or small molecules.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A method of quantitating the concentration of a molecule of interest comprising:
   identifying, for a first and a second test site, a respective capturing agent recipe, wherein the capturing agent recipe for each of the first and the second test sites is different from the capturing agent recipe for the other of the first and the second test sites;
   immobilizing, in each of the first and the second test sites, a first capturing agent in accordance with the identified recipe;
   establishing a first test environment at the first test site;
   establishing a second test environment at the second test site such that a response curve for the second site is different from a response curve of the first site;
   storing a combined response curve resulting from a summation of the response curve for the second site and the response curve of the first site;
   exposing the first test site and the second test site to a sample having a concentration of a molecule of interest;
   obtaining a first quantitation signal from the first test site;
   obtaining a second quantitation signal from the second test site;
   combining the first quantitation signal and the second quantitation signal;
   associating the combined first quantitation signal and second quantitation signal with the stored response curve; and
   determining the concentration of the molecule of interest based upon the association.

2. The method of claim 1, wherein the first capturing agent is a first of a plurality of capturing agents, each of the plurality of capturing agents exhibiting an affinity to the molecule of interest that is different from the affinity to the molecule of interest of another of the plurality of capturing agents.

3. The method of claim 1, wherein the response curve of the first site overlaps the response curve of the second site.

4. The method of claim 1, wherein:
   establishing a first test environment includes controlling at least one environmental factor of a group of environmental factors consisting of temperature, electric field, magnetic field, and pH, for the first test site; and
   establishing a second test environment includes controlling the at least one environmental factor for the second test site, such that the controlled at least one environmental factor is different between the first test site and the second test site.

5. A method of quantitating the concentration of a molecule of interest comprising:
   forming a first test site and a second test site with a first capturing agent in a respective well of a multi-well plate;
   establishing a first test environment at the first test site;
   establishing a second test environment at the second test site such that a response curve for the second site is different from a response curve of the first site;
   storing a combined response curve resulting from a summation of the response curve for the second site and the response curve of the first site;
   exposing the first test site and the second test site to a sample having a concentration of a molecule of interest;
   obtaining a first quantitation signal from the first test site;
   obtaining a second quantitation signal from the second test site;
   combining the first quantitation signal and the second quantitation signal;
   associating the combined first quantitation signal and second quantitation signal with the stored response curve; and
   determining the concentration of the molecule of interest based upon the association.

6. The method of claim 5, wherein the response curve of the first site overlaps the response curve of the second site.

7. The method of claim 5, wherein:
   establishing a first test environment includes controlling at least one environmental factor of a group of environmental factors consisting of temperature, electric field, magnetic field, and pH, for the first test site; and
   establishing a second test environment includes controlling the at least one environmental factor for the second test site, such that the controlled at least one environmental factor is different between the first test site and the second test site.

8. A method of quantitating the concentration of a molecule of interest comprising:
   forming a first test site and a second test site with a first capturing agent on a CMOS substrate;
   establishing a first test environment at the first test site;
   establishing a second test environment at the second test site such that a response curve for the second site is different from a response curve of the first site;
   storing a combined response curve resulting from a summation of the response curve for the second site and the response curve of the first site;
   exposing the first test site and the second test site to a sample having a concentration of a molecule of interest;
   obtaining a first quantitation signal from the first test site;
   obtaining a second quantitation signal from the second test site;
   combining the first quantitation signal and the second quantitation signal;
   associating the combined first quantitation signal and second quantitation signal with the stored response curve; and
   determining the concentration of the molecule of interest based upon the association.

9. The method of claim 8, wherein the response curve of the first site overlaps the response curve of the second site.

10. The method of claim 8, wherein:
    establishing a first test environment includes controlling at least one environmental factor of a group of environmental factors consisting of temperature, electric field, magnetic field, and pH, for the first test site; and
    establishing a second test environment includes controlling the at least one environmental factor for the second test site, such that the controlled at least one environmental factor is different between the first test site and the second test site.

* * * * *